(12) United States Patent
Aranyi

(10) Patent No.: US 11,337,692 B2
(45) Date of Patent: May 24, 2022

(54) APPARATUS FOR ENDOSCOPIC PROCEDURES

(71) Applicant: Covidien LP, Mansfield, MA (US)

(72) Inventor: Ernest Aranyi, Easton, CT (US)

(73) Assignee: COVIDIEN LP, Mansfield, MA (US)

( * ) Notice: Subject to any disclaimer, the term of this patent is extended or adjusted under 35 U.S.C. 154(b) by 328 days.

(21) Appl. No.: 16/732,941

(22) Filed: Jan. 2, 2020

(65) Prior Publication Data

US 2020/0138432 A1 May 7, 2020

Related U.S. Application Data

(63) Continuation of application No. 15/428,624, filed on Feb. 9, 2017, now Pat. No. 10,542,973, which is a
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 2017/00314* (2013.01); *A61B 2017/00398* (2013.01); *A61B 2017/00473* (2013.01); *A61B 2017/00734* (2013.01); *A61B 2017/07214* (2013.01); *A61B 2017/07285* (2013.01); *A61B 2017/2927* (2013.01)

(58) Field of Classification Search
CPC .......................... A61B 17/07207; A61B 17/068
USPC ....................................................... 227/177.1
See application file for complete search history.

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

CA 2451558 A1 1/2003
CN 102247182 A 11/2011
(Continued)

OTHER PUBLICATIONS

Canadian Office Action for application No. 2873238 dated Jan. 29, 2021.
(Continued)

*Primary Examiner* — Dariush Seif
(74) *Attorney, Agent, or Firm* — Carter, DeLuca & Farrell LLP

(57) ABSTRACT

A surgical stapling apparatus includes a handle assembly, a shaft assembly extending distally from the handle assembly, and an end effector selectively detachable from the shaft assembly. The end effector includes a first jaw member and a second jaw member. The first jaw member supports a lever that is pivotally movable relative to the first jaw member between an extended position and a retracted position. The lever is in contact with a leaf spring to spring bias the lever to the extended position. The second jaw member supports a drive beam that is selectively engagable with the lever to facilitate a pivotal movement of the second jaw member relative to the first jaw member between an unapproximated state and an approximated state.

20 Claims, 9 Drawing Sheets

Related U.S. Application Data continuation of application No. 14/161,092, filed on Jan. 22, 2014, now Pat. No. 9,655,616.

(51) Int. Cl.
*A61B 17/00* (2006.01)
*A61B 17/29* (2006.01)

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,874,181 A | 10/1989 | Hsu | |
| 5,074,454 A * | 12/1991 | Peters | A61B 17/07207 227/178.1 |
| 5,129,118 A | 7/1992 | Walmesley | |
| 5,129,570 A | 7/1992 | Schulze et al. | |
| 5,152,744 A | 10/1992 | Krause et al. | |
| 5,307,976 A * | 5/1994 | Olson | A61B 17/07207 227/175.3 |
| 5,312,023 A * | 5/1994 | Green | A61B 17/07207 227/175.1 |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,392,978 A * | 2/1995 | Velez | A61B 17/0644 227/175.1 |
| 5,395,033 A | 3/1995 | Byrne et al. | |
| 5,400,267 A | 3/1995 | Denen et al. | |
| 5,413,267 A | 5/1995 | Solyntjes et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,507,773 A * | 4/1996 | Huitema | A61B 17/07207 600/564 |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,542,594 A | 8/1996 | McKean et al. | |
| 5,562,239 A | 10/1996 | Boiarski et al. | |
| 5,653,374 A | 8/1997 | Young et al. | |
| 5,665,100 A * | 9/1997 | Yoon | A61B 10/06 606/139 |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,779,130 A | 7/1998 | Alesi et al. | |
| 5,782,397 A | 7/1998 | Koukline | |
| 5,797,958 A * | 8/1998 | Yoon | A61B 17/122 606/139 |
| 5,820,009 A | 10/1998 | Melling et al. | |
| 5,863,159 A | 1/1999 | Lasko | |
| 5,893,863 A * | 4/1999 | Yoon | A61B 18/1442 606/170 |
| 5,908,427 A | 6/1999 | McKean et al. | |
| 5,919,202 A * | 7/1999 | Yoon | A61B 17/1285 606/170 |
| 5,954,259 A | 9/1999 | Viola et al. | |
| 5,964,774 A | 10/1999 | McKean et al. | |
| 5,993,454 A | 11/1999 | Longo | |
| 6,017,354 A | 1/2000 | Culp et al. | |
| 6,032,849 A * | 3/2000 | Mastri | A61B 17/07207 227/176.1 |
| 6,045,560 A | 4/2000 | McKean et al. | |
| 6,090,123 A | 7/2000 | Culp et al. | |
| 6,129,547 A | 10/2000 | Cise et al. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,792,390 B1 | 9/2004 | Burnside et al. | |
| 6,817,508 B1 | 11/2004 | Racenet et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 7,032,798 B2 | 4/2006 | Whitman et al. | |
| 7,055,731 B2 | 6/2006 | Shelton, IV et al. | |
| 7,077,856 B2 | 7/2006 | Whitman | |
| 7,111,769 B2 | 9/2006 | Wales et al. | |
| 7,128,253 B2 * | 10/2006 | Mastri | A61B 17/0684 227/176.1 |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,225,963 B2 * | 6/2007 | Scirica | A61B 17/072 227/175.1 |
| 7,246,734 B2 | 7/2007 | Shelton, IV | |
| 7,328,828 B2 | 2/2008 | Ortiz et al. | |
| 7,364,061 B2 | 4/2008 | Swayze et al. | |
| 7,380,695 B2 * | 6/2008 | Doll | A61B 17/07207 227/175.1 |
| 7,380,696 B2 | 6/2008 | Shelton, IV et al. | |
| 7,404,508 B2 | 7/2008 | Smith et al. | |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,467,740 B2 * | 12/2008 | Shelton, IV | A61B 17/07207 227/178.1 |
| 7,481,347 B2 | 1/2009 | Roy | |
| 7,487,899 B2 | 2/2009 | Shelton, IV et al. | |
| 7,549,564 B2 | 6/2009 | Boudreaux | |
| 7,568,603 B2 | 8/2009 | Shelton, IV et al. | |
| 7,588,176 B2 | 9/2009 | Timm et al. | |
| 7,637,409 B2 | 12/2009 | Marczyk | |
| 7,641,093 B2 | 1/2010 | Doll et al. | |
| 7,644,848 B2 | 1/2010 | Swayze et al. | |
| 7,670,334 B2 | 3/2010 | Hueil et al. | |
| 7,673,780 B2 | 3/2010 | Shelton, IV et al. | |
| 7,721,931 B2 | 5/2010 | Shelton, IV et al. | |
| 7,740,159 B2 | 6/2010 | Shelton, IV et al. | |
| 7,743,960 B2 | 6/2010 | Whitman et al. | |
| 7,758,613 B2 | 7/2010 | Whitman | |
| 7,766,210 B2 | 8/2010 | Shelton, IV et al. | |
| 7,770,773 B2 | 8/2010 | Whitman et al. | |
| 7,770,775 B2 | 8/2010 | Shelton, IV et al. | |

(56) References Cited

U.S. PATENT DOCUMENTS

| | | |
|---|---|---|
| 7,799,039 B2 | 9/2010 | Shelton, IV et al. |
| 7,802,712 B2 | 9/2010 | Milliman et al. |
| 7,845,537 B2 | 12/2010 | Shelton, IV et al. |
| 7,905,897 B2 | 3/2011 | Whitman et al. |
| 7,918,230 B2 | 4/2011 | Whitman et al. |
| 7,947,034 B2 | 5/2011 | Whitman |
| 7,951,071 B2 | 5/2011 | Whitman et al. |
| 7,963,433 B2 | 6/2011 | Whitman et al. |
| 7,967,178 B2 | 6/2011 | Scirica et al. |
| 7,992,758 B2 | 8/2011 | Whitman et al. |
| 8,016,855 B2 | 9/2011 | Whitman et al. |
| 8,020,743 B2 | 9/2011 | Shelton, IV |
| 8,114,118 B2 | 2/2012 | Knodel et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,220,367 B2 | 7/2012 | Hsu |
| 8,241,322 B2 | 8/2012 | Whitman et al. |
| 8,292,150 B2 | 10/2012 | Bryant |
| 8,292,888 B2 | 10/2012 | Whitman |
| 8,357,144 B2 | 1/2013 | Whitman et al. |
| 8,365,972 B2 | 2/2013 | Aranyi et al. |
| 8,372,057 B2 | 2/2013 | Cude et al. |
| 8,391,957 B2 | 3/2013 | Carlson et al. |
| 8,517,241 B2 | 8/2013 | Nicholas et al. |
| 8,657,177 B2 | 2/2014 | Scirica et al. |
| 8,672,206 B2 | 3/2014 | Aranyi et al. |
| 9,636,112 B2 | 5/2017 | Penna et al. |
| 10,542,973 B2 | 1/2020 | Aranyi |
| 2002/0062136 A1* | 5/2002 | Hillstead .......... A61B 17/07207 606/205 |
| 2002/0066764 A1* | 6/2002 | Perry ................ A61B 17/072 227/175.2 |
| 2003/0045900 A1* | 3/2003 | Hahnen ............ A61B 17/07207 606/205 |
| 2003/0120287 A1* | 6/2003 | Gross ................ A61B 17/0469 606/148 |
| 2003/0181926 A1* | 9/2003 | Dana ................. A61B 17/0485 606/148 |
| 2004/0111012 A1 | 6/2004 | Whitman |
| 2004/0164123 A1* | 8/2004 | Racenet ............ A61B 17/072 227/176.1 |
| 2005/0184125 A1* | 8/2005 | Marczyk .......... A61B 17/07207 227/176.1 |
| 2005/0256533 A1* | 11/2005 | Roth ................. A61F 5/0083 606/167 |
| 2006/0142656 A1 | 6/2006 | Malackowski et al. |
| 2006/0278680 A1 | 12/2006 | Viola et al. |
| 2007/0023477 A1* | 2/2007 | Whitman ............ A61B 34/71 227/175.1 |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0158384 A1* | 7/2007 | Zins .................. B25C 11/00 227/132 |
| 2007/0175949 A1 | 8/2007 | Shelton et al. |
| 2007/0175950 A1* | 8/2007 | Shelton ............ A61B 17/07207 227/176.1 |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0185419 A1 | 8/2008 | Smith et al. |
| 2008/0208195 A1 | 8/2008 | Shores et al. |
| 2008/0237297 A1 | 10/2008 | Demmy et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0306342 A1* | 12/2008 | Leonard ............ A61B 17/2909 600/131 |
| 2008/0308601 A1* | 12/2008 | Timm ............... A61B 17/07207 227/175.1 |
| 2009/0090763 A1 | 4/2009 | Zemlok et al. |
| 2009/0099876 A1 | 4/2009 | Whitman |
| 2009/0101692 A1* | 4/2009 | Whitman ............ A61B 17/068 227/175.1 |
| 2009/0138006 A1 | 5/2009 | Bales et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0225073 A1 | 9/2010 | Porter et al. |
| 2010/0292739 A1* | 11/2010 | Schwab ............ A61B 17/7034 606/305 |
| 2011/0077673 A1 | 3/2011 | Grubac et al. |
| 2011/0112569 A1* | 5/2011 | Friedman ............ A61B 5/283 606/205 |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0174099 A1 | 7/2011 | Ross et al. |
| 2011/0174862 A1* | 7/2011 | Shelton, IV ...... A61B 17/07207 227/176.1 |
| 2011/0184404 A1* | 7/2011 | Walberg ............ A61B 18/1445 606/33 |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0290853 A1* | 12/2011 | Shelton, IV ......... A61B 17/068 227/177.1 |
| 2011/0290854 A1* | 12/2011 | Timm ................ A61B 17/072 227/178.1 |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0080493 A1* | 4/2012 | Shelton, IV ...... A61B 17/07292 227/176.1 |
| 2012/0080496 A1* | 4/2012 | Schall ............... A61B 17/07292 227/177.1 |
| 2012/0089131 A1 | 4/2012 | Zemlok et al. |
| 2012/0104072 A1* | 5/2012 | Vidal ................ A61B 17/07207 227/176.1 |
| 2012/0138660 A1* | 6/2012 | Shelton, IV ........... A61B 34/71 227/176.1 |
| 2012/0143002 A1 | 6/2012 | Aranyi et al. |
| 2012/0223121 A1 | 9/2012 | Viola et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2013/0018361 A1 | 1/2013 | Bryant |
| 2013/0030462 A1* | 1/2013 | Keating ................ A61B 17/29 606/206 |
| 2013/0098966 A1 | 4/2013 | Kostrzewski et al. |
| 2013/0098968 A1* | 4/2013 | Aranyi ............... A61B 17/07292 227/177.1 |
| 2013/0098969 A1 | 4/2013 | Scirica et al. |
| 2013/0153636 A1* | 6/2013 | Shelton, IV ......... A61B 17/068 227/176.1 |
| 2013/0161374 A1* | 6/2013 | Swayze ............... A61B 17/068 227/176.1 |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0306703 A1* | 11/2013 | Ehrenfels ............ A61B 17/105 227/175.2 |
| 2013/0313305 A1* | 11/2013 | Scirica ............. A61B 17/07207 227/180.1 |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |

(56) References Cited

U.S. PATENT DOCUMENTS

| | | | |
|---|---|---|---|
| 2014/0012236 A1 | 1/2014 | Williams et al. | |
| 2014/0012237 A1 | 1/2014 | Pribanic et al. | |
| 2014/0012289 A1 | 1/2014 | Snow et al. | |
| 2014/0025046 A1 | 1/2014 | Williams et al. | |
| 2014/0214025 A1* | 7/2014 | Worrell | A61B 18/1445 606/41 |
| 2014/0246471 A1* | 9/2014 | Jaworek | A61B 34/30 227/175.1 |
| 2014/0263566 A1* | 9/2014 | Williams | A61B 17/068 227/180.1 |
| 2015/0173756 A1* | 6/2015 | Baxter, III | A61B 17/064 227/177.1 |
| 2015/0201930 A1* | 7/2015 | Aranyi | A61B 17/068 227/177.1 |
| 2015/0374361 A1* | 12/2015 | Gettinger | A61B 17/068 227/175.2 |
| 2017/0143339 A1* | 5/2017 | Aranyi | A61B 17/07207 |
| 2020/0138432 A1* | 5/2020 | Aranyi | A61B 17/07207 |

FOREIGN PATENT DOCUMENTS

| | | |
|---|---|---|
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 1690502 A1 | 8/2006 |
| EP | 1736112 A1 | 12/2006 |
| EP | 1769754 A1 | 4/2007 |
| EP | 1813199 A1 | 8/2007 |
| EP | 1813203 A2 | 8/2007 |
| EP | 1813211 A2 | 8/2007 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2055243 A2 | 5/2009 |
| EP | 2098170 A2 | 9/2009 |
| EP | 2100561 A2 | 9/2009 |
| EP | 2165664 A2 | 3/2010 |
| EP | 2236098 A2 | 10/2010 |
| EP | 2263568 A2 | 12/2010 |
| EP | 2329773 A1 | 6/2011 |
| EP | 2333509 A1 | 6/2011 |
| EP | 2462880 B1 | 6/2012 |
| EP | 2491872 A1 | 8/2012 |
| EP | 2586382 A2 | 5/2013 |
| EP | 2606834 A2 | 6/2013 |
| EP | 2676615 A2 | 12/2013 |
| JP | H09164144 A | 6/1997 |
| JP | 2005160889 A | 6/2005 |
| JP | 2009112782 A | 5/2009 |
| JP | 2013244401 A | 12/2013 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03077769 A1 | 9/2003 |
| WO | 2004107989 A1 | 12/2004 |
| WO | 2006042210 A2 | 4/2006 |
| WO | 2007026354 A1 | 3/2007 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2011007351 A1 | 1/2011 |
| WO | 2011108840 A2 | 9/2011 |

OTHER PUBLICATIONS

Chinese Office Action issued in Chinese Application No. 201410844258X dated May 9, 2018.
Australian Office Action issued in Australian Application No. 2014256425 dated Aug. 27, 2018.
Japanese Office Action issued in corresponding Japanese Application No. 2014-248847 dated Sep. 18, 2018.
International Search Report corresponding to PCT/US2005/027266, completed May 30, 2008 and dated Jun. 18, 2008 (2 pp.).
Extended European Search Report corresponding to EP 08 25 2703.7, completed Oct. 23, 2008 and dated Oct. 31, 2008; (7 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013 (6 pp.).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report corresponding to EP 15 16 6762.3 dated Jul. 16, 2015; 7 pp.
European Search Report corresonding to 14 19 9697.5 dated Jun. 26, 2015; 4 pp.

* cited by examiner

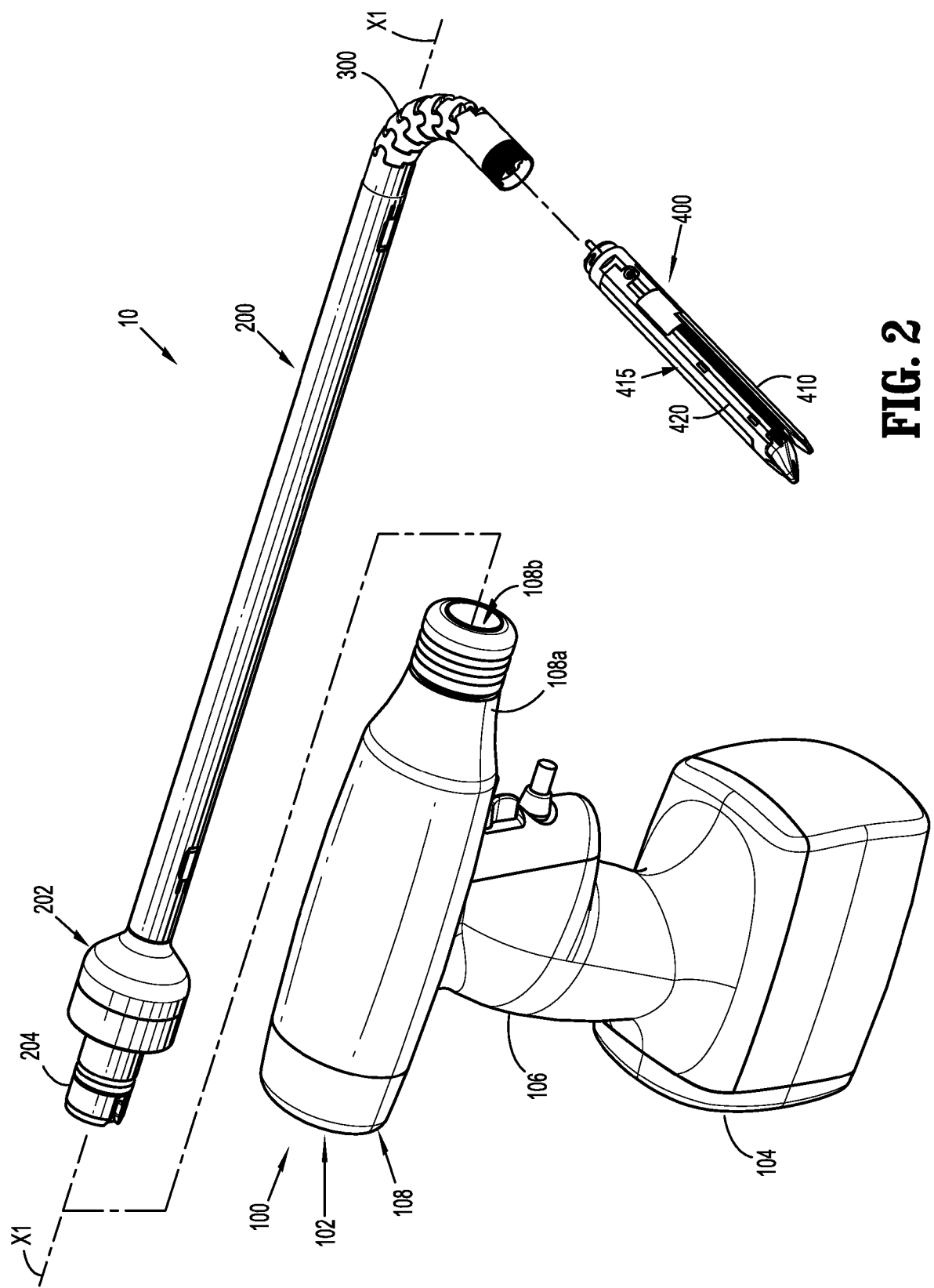

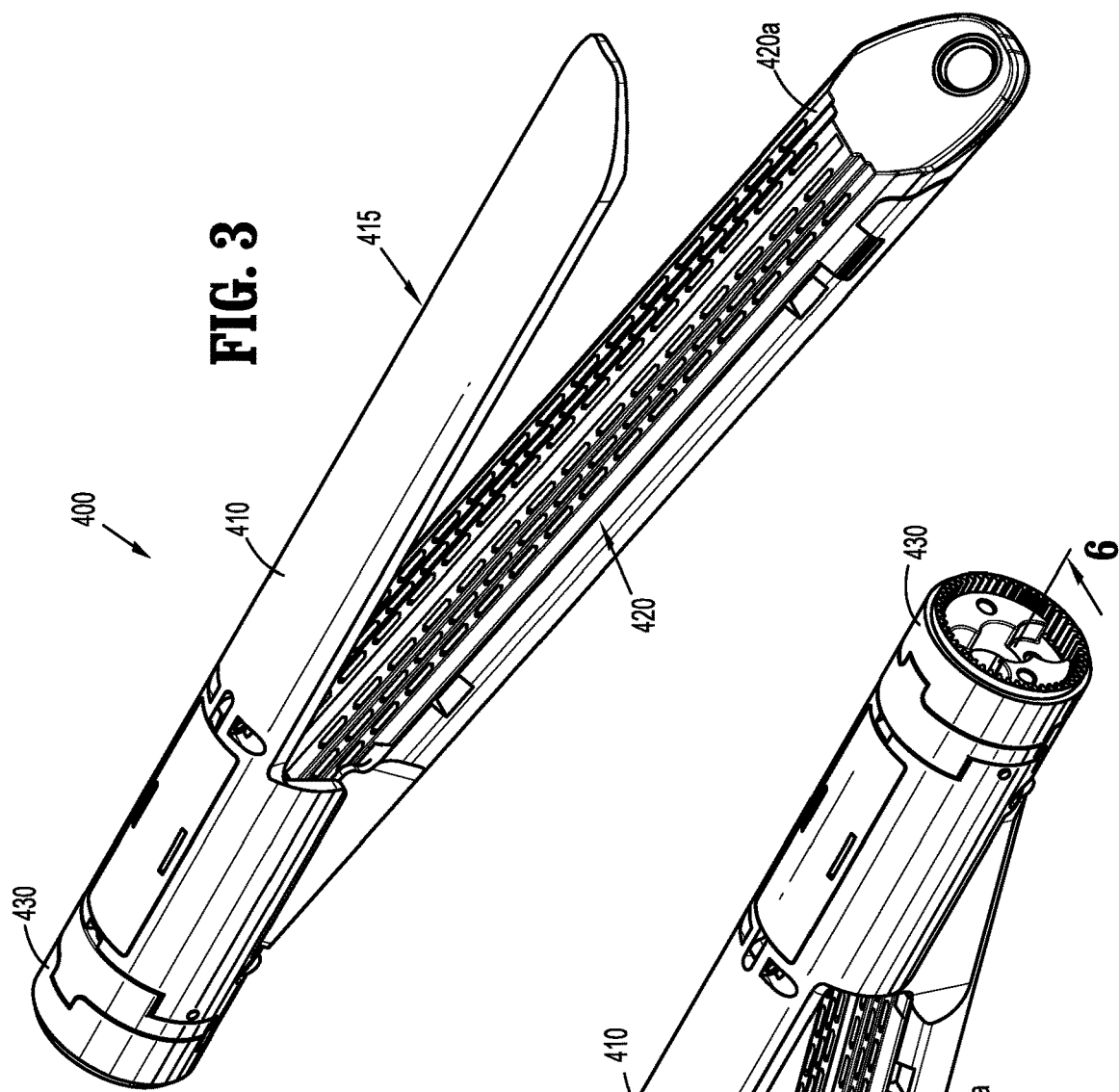
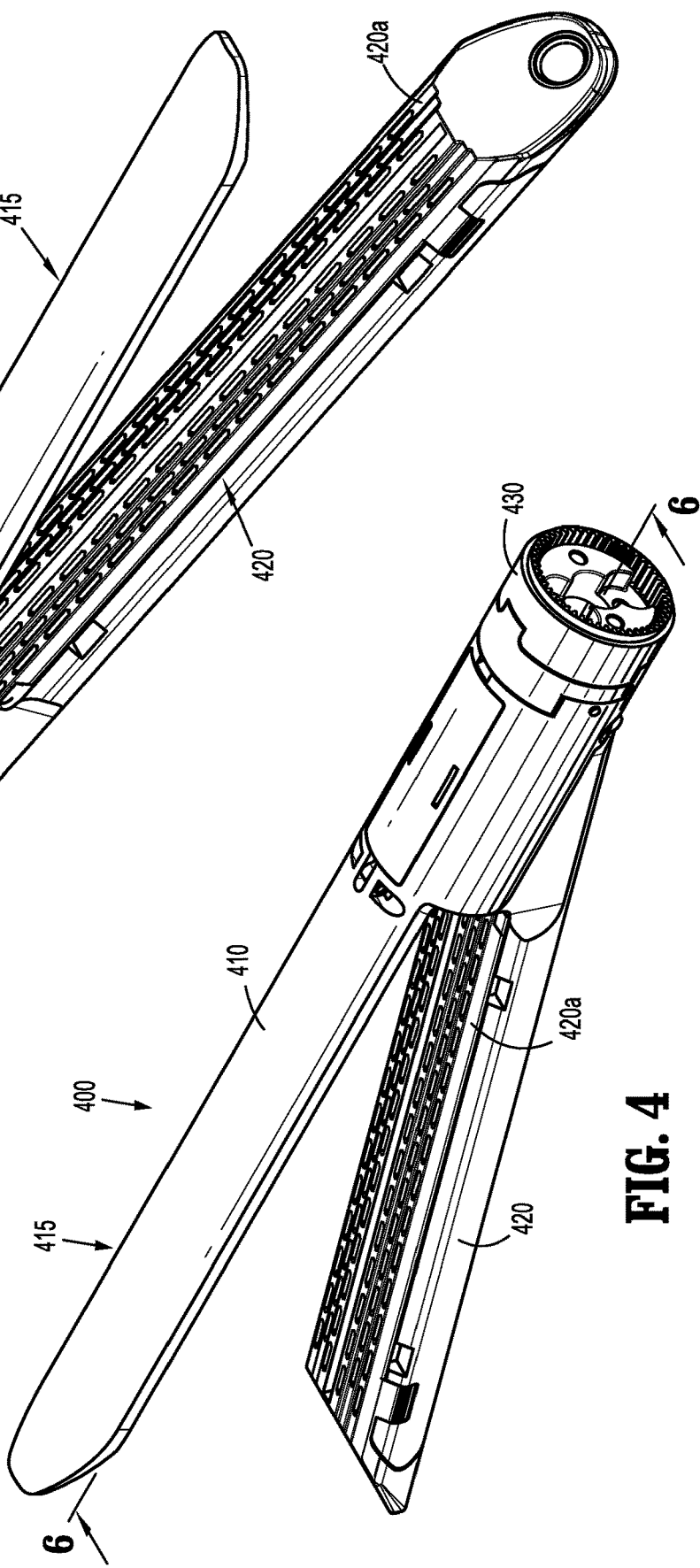

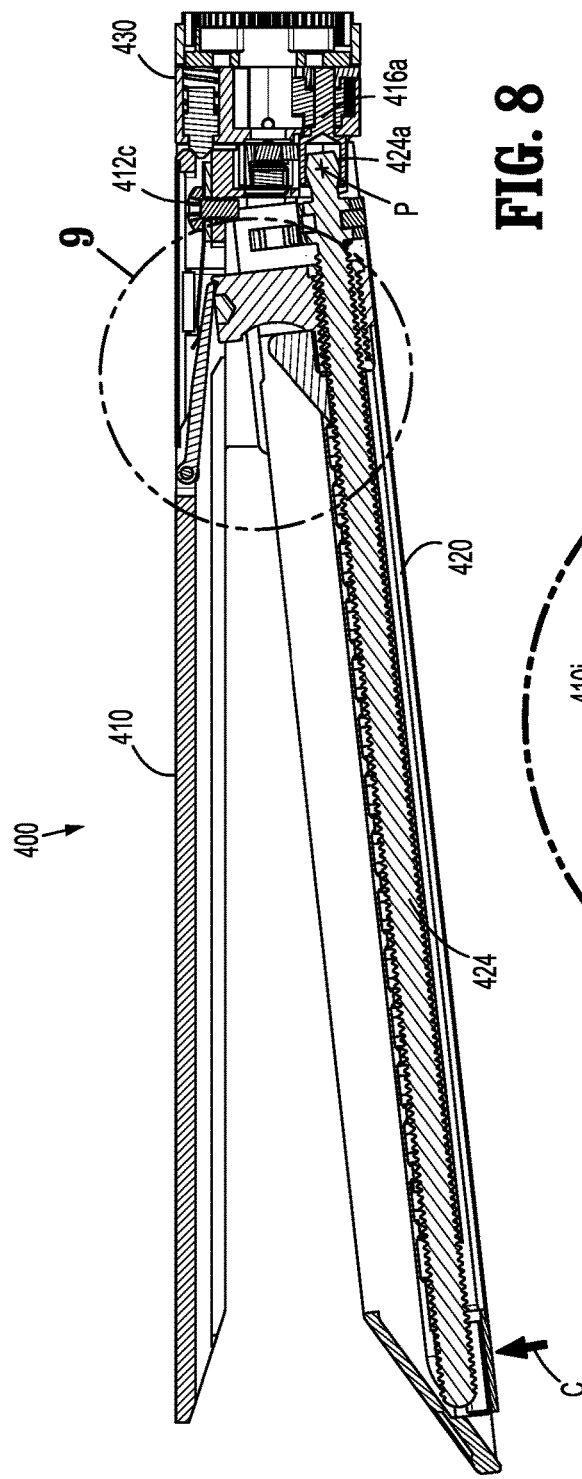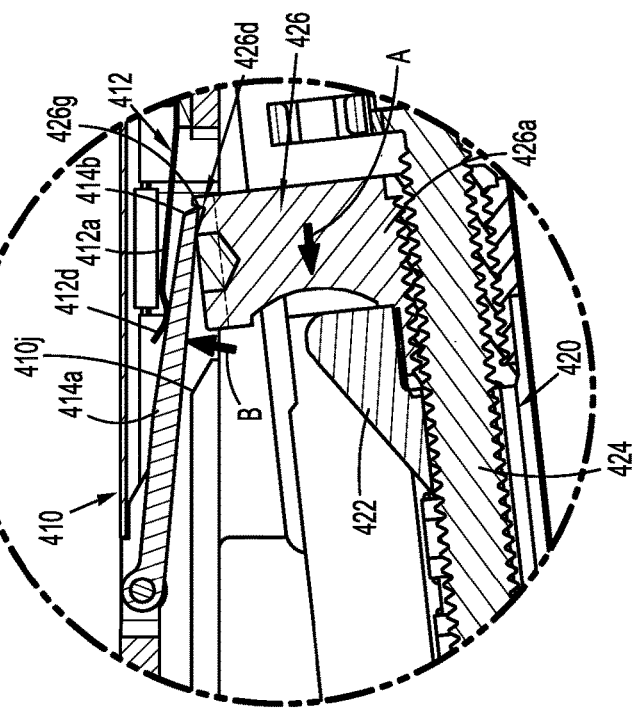
FIG. 8
FIG. 9

APPARATUS FOR ENDOSCOPIC PROCEDURES

CROSS REFERENCE TO RELATED APPLICATIONS

This application is a continuation of U.S. patent application Ser. No. 15/428,624, filed Feb. 9, 2017, which is a continuation of Ser. No. 14/161,092, filed Jan. 22, 2014 now U.S. Pat. No. 9,655,616, the entire contents of each of which are incorporated by reference herein.

TECHNICAL FIELD

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting, and/or stapling tissue.

BACKGROUND

A number of surgical device manufacturers have developed product lines with proprietary drive systems for operating and/or manipulating electromechanical surgical devices. Some electromechanical surgical devices include a handle assembly, which is reusable, and replaceable loading units and/or single use loading units or the like that are selectively connected to the handle assembly prior to use and then disconnected from the handle assembly following use, in order to be disposed of or in some instances sterilized for re-use.

Many of these electromechanical surgical devices are relatively expensive to manufacture, purchase, and/or operate. There is a desire by manufactures and end users to develop electromechanical surgical devices that are relatively inexpensive to manufacture, purchase, and/or operate.

Accordingly, a need exists for electromechanical surgical apparatus, devices and/or systems that are relatively economical to develop and manufacture, to store and ship, as well as economical and convenient to purchase and use from the end user's perspective.

SUMMARY

According to one aspect of the present disclosure, an end effector includes a mounting portion and first and second jaw members that extend distally from the mounting portion. A fastener cartridge is secured to the second jaw member. The fastener cartridge supports a plurality of fasteners in fastener retaining slots defined in a tissue engaging surface of the fastener cartridge.

In another aspect, a surgical stapling apparatus includes a handle assembly, a shaft assembly extending distally from the handle assembly, and an end effector selectively detachable from the shaft assembly. In embodiments the surgical stapling apparatus is powered.

The first jaw member includes a tissue engaging surface and may support a lever assembly. The second jaw member may support a drive beam that is selectively engagable with the lever assembly to facilitate a pivotal movement of the second jaw member relative to the first jaw member between an unapproximated state and an approximated state. The first jaw member may define a ramp. The drive beam may be engagable with the ramp to pivot the first jaw member and the second jaw member to the approximated state and enable the drive beam to distally translate along the first and second jaw members.

The drive beam may configured to disengage from the lever assembly, to distally translate along the first jaw member and the second jaw member to approximate the first and second jaw members relative to one another, and distally translate along the fastener cartridge to fire the plurality of fasteners from the fastener retaining slots and form the plurality of fasteners against the tissue engaging surface of the first jaw member. The drive beam may define a notch therein and may support a knife adapted to cut tissue as the drive beam translates along the fastener cartridge.

The lever assembly may include a lever pivotally connected to the first jaw member and pivotally movable relative to the first jaw member between an extended position and a retracted position. The lever may be engaged with the notch of the drive beam when the first and second jaw members are in the unapproximated state, when the drive beam is in a proximal position, and when the lever is in the extended position. The lever may be engaged with the notch of the drive beam to limit distal translation of the drive beam prior to the second jaw member pivoting relative to the first jaw member from the unapproximated state to the approximated state. The lever may be configured to disengage from the notch as the lever pivots from the extended position to the retracted position in response to the second jaw member pivoting relative to the first jaw member from the unapproximated state to the approximated state. The drive beam may be distally translatable when the first and second jaw members are in the approximated state and the lever is in the retracted position.

A spring assembly may be supported by the first jaw member. The spring assembly may include a spring configured to contact the lever to bias the lever to the extended position. The spring may be a leaf spring.

A drive screw may be supported by the second jaw member that is operably associated with the drive beam to translate the drive beam as the drive screw rotates. The drive beam may include a retention foot that threadably receives the drive screw. The drive screw may be coupled to a rotatable drive member, wherein rotation of the drive screw in the retention foot facilitates pivotal movement of the second jaw member relative to the first jaw member and translation of the drive beam through the fastener cartridge. The drive screw may have a head projecting from a proximal end portion thereof. The head may define a pivot axis therethrough that is transverse to a longitudinal axis of the end effector between proximal and distal end portions of the end effector. The second jaw member may be configured to pivot relative to the first jaw member about the pivot axis.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 2 is a perspective view, with parts separated, of the electromechanical surgical system of FIG. 1;

FIG. 3 is a front, perspective view of an end effector of the electromechanical surgical system of FIGS. 1 and 2;

FIG. 4 is a rear, perspective view of the end effector of FIG. 3;

FIG. 8 is a side, cross-sectional view of the end effector showing a drive beam thereof in a partially advanced position;

FIG. 9 is an enlarged view of the indicated area of detail shown in FIG. 8;

DETAILED DESCRIPTION

Figure 1:
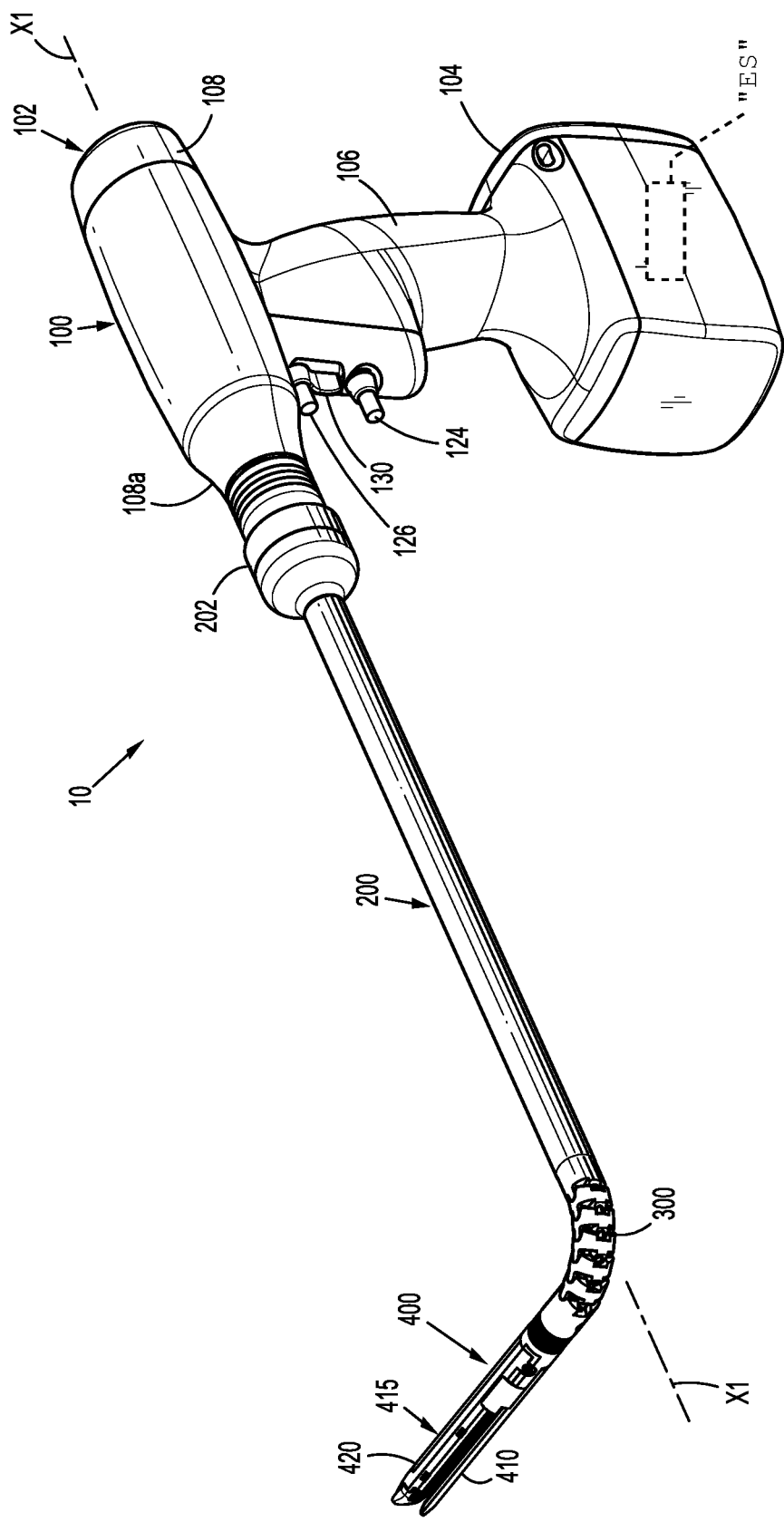
FIG. 1 is a perspective view of an electromechanical surgical system according to the principles of the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Referring initially to FIGS. 1 and 2, an electromechanical, hand-held, powered surgical system is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200, that are each configured for actuation and manipulation by the electromechanical, hand-held, powered surgical instrument 100. In particular, surgical instrument 100 is configured for selective connection with an articulation assembly 300 of shaft assembly 200, and, in turn, shaft assembly 200 is configured for selective connection with any one of a plurality of different end effectors 400 via articulation assembly 300.

Reference may be made to U.S. Patent Application Publication No. 2009/0101692, U.S. Patent Application Publication No. 2011/0121049, and U.S. Patent Application Publication No. 2013/0098966, the entire content of each of which is hereby incorporated herein by reference, for a detailed description of the construction and operation of exemplary electromechanical, hand-held, powered surgical instruments, the components of which are combinable and/or interchangeable with one or more components of powered surgical system 10 described herein.

Generally, as illustrated in FIGS. 1 and 2, surgical instrument 100 includes an instrument housing 102 having a lower housing portion 104, an intermediate housing portion 106 extending from and/or supported on lower housing portion 104, and an upper housing portion 108 extending from and/or supported on intermediate housing portion 106. The surgical instrument 100 has a controller (not shown) for controlling certain functions of the surgical system, collecting data, and performing other functions. Instrument housing 102 defines a cavity (not shown) therein in which a circuit board (not shown) and a drive mechanism (not shown) are situated.

The circuit board is configured to control the various operations of surgical instrument 100, as will be set forth in additional detail below. In accordance with the present disclosure, instrument housing 102 provides a housing in which an electrical source "ES," such as a battery, is removably situated (see FIG. 1). The battery may be rechargeable. The battery is configured to supply electrical power to any of the electrical components of surgical instrument 100.

Upper housing portion 108 of instrument housing 102 has a nose or connecting portion 108a configured to accept a corresponding shaft coupling assembly 204 of transmission housing 202 of shaft assembly 200. As seen in FIG. 2, connecting portion 108a of upper housing portion 108 of surgical instrument 100 defines a cylindrical recess 108b that receives shaft coupling assembly 204 of transmission housing 202 of shaft assembly 200 when shaft assembly 200 is mated to surgical instrument 100. The connecting portion 108a of the surgical instrument 100 has at least one rotatable drive member. In some embodiments, connecting portion 108a houses a plurality of rotatable drive members or connectors (not shown), each drive member of the plurality of drive members can be independently, and/or dependently, actuatable and rotatable by the drive mechanism (not shown) housed within instrument housing 102.

Upper housing portion 108 of instrument housing 102 provides a housing in which the drive mechanism (not shown) is situated. The drive mechanism is configured to drive shafts and/or gear components in order to perform the various operations of surgical instrument 100. In particular, the drive mechanism is configured to drive shafts and/or gear components in order to selectively move end effector 400 relative to shaft assembly 200; to rotate anvil assembly 200 and/or end effector 400, about a longitudinal axis "X1" (see FIGS. 1 and 2), relative to instrument housing 102; to move an upper jaw member or anvil assembly 410 of end effector 400 relative to a lower jaw member or cartridge assembly 420 of end effector 400; to articulate and/or rotate the shaft assembly 200; and/or to fire a fastener cartridge 420a within cartridge assembly 420 of end effector 400.

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive members or connectors of surgical instrument 100, at a given time.

As illustrated in FIGS. 1 and 2, instrument housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator. In addition, the circuit board (not shown) housed in instrument housing 102 includes, for each one of the control buttons 124, 126 and rocker device(s) 130, respective Hall-effect switches (not shown) that are actuated by the movement of the magnets in the control buttons 124, 126 and rocker device(s) 130. The actuation of Hall-effect switch (not shown), corresponding to control buttons 124, 126 causes the circuit board to provide appropriate signals to the function selection module and the input drive component of the drive mechanism to open/close end effector 400 and/or to fire a stapling/cutting cartridge within end effector 400.

Similarly, the actuation of the Hall-effect switch, corresponding to rocker device 130, causes the circuit board to provide appropriate signals to the function selection module and the input drive component of the drive mechanism to rotate end effector 400 relative to shaft assembly 200 or rotate end effector 400 and shaft assembly 200 relative to instrument housing 102 of surgical instrument 100. Specifically, movement of rocker device 130 in a first direction causes end effector 400 and/or shaft assembly 200 to rotate relative to instrument housing 102 in a first direction, while movement of rocker device 130 in an opposite, e.g., second, direction causes end effector 400 and/or shaft assembly 200 to rotate relative to instrument housing 102 in an opposite, e.g., second, direction.

Turning now to FIGS. 3-13, end effector 400 is shown and described. End effector 400 is configured and adapted to apply a plurality of linear rows of fasteners "F" (e.g., staples, see FIG. 5). In certain embodiments, the fasteners are of various sizes, and, in certain embodiments, the fasteners have various lengths or rows, e.g., about 30, 45 and 60 mm in length.

As seen in FIGS. 3 and 4, end effector 400 includes a mounting portion 430 coupled to a jaw assembly 415. A proximal end portion of mounting portion 430 is configured for selective connection to a distal end portion of shaft assembly 200 (e.g., articulation assembly 300) that has complementary structure formed thereon. Jaw assembly 415 is connected to, and extends distally from, mounting portion 430. Jaw assembly 415, as will be discussed in greater detail below, includes lower jaw member 420, which is configured to selectively support fastener cartridge 420a therein, and upper jaw member 410, each of which is secured to mounting portion 430 to enable relative movement between upper and lower jaw members 410, 420. Jaw assembly 415 is pivotally movable to orient upper and lower jaw members 410, 420 between approximated and unapproximated states.

Figure 5:
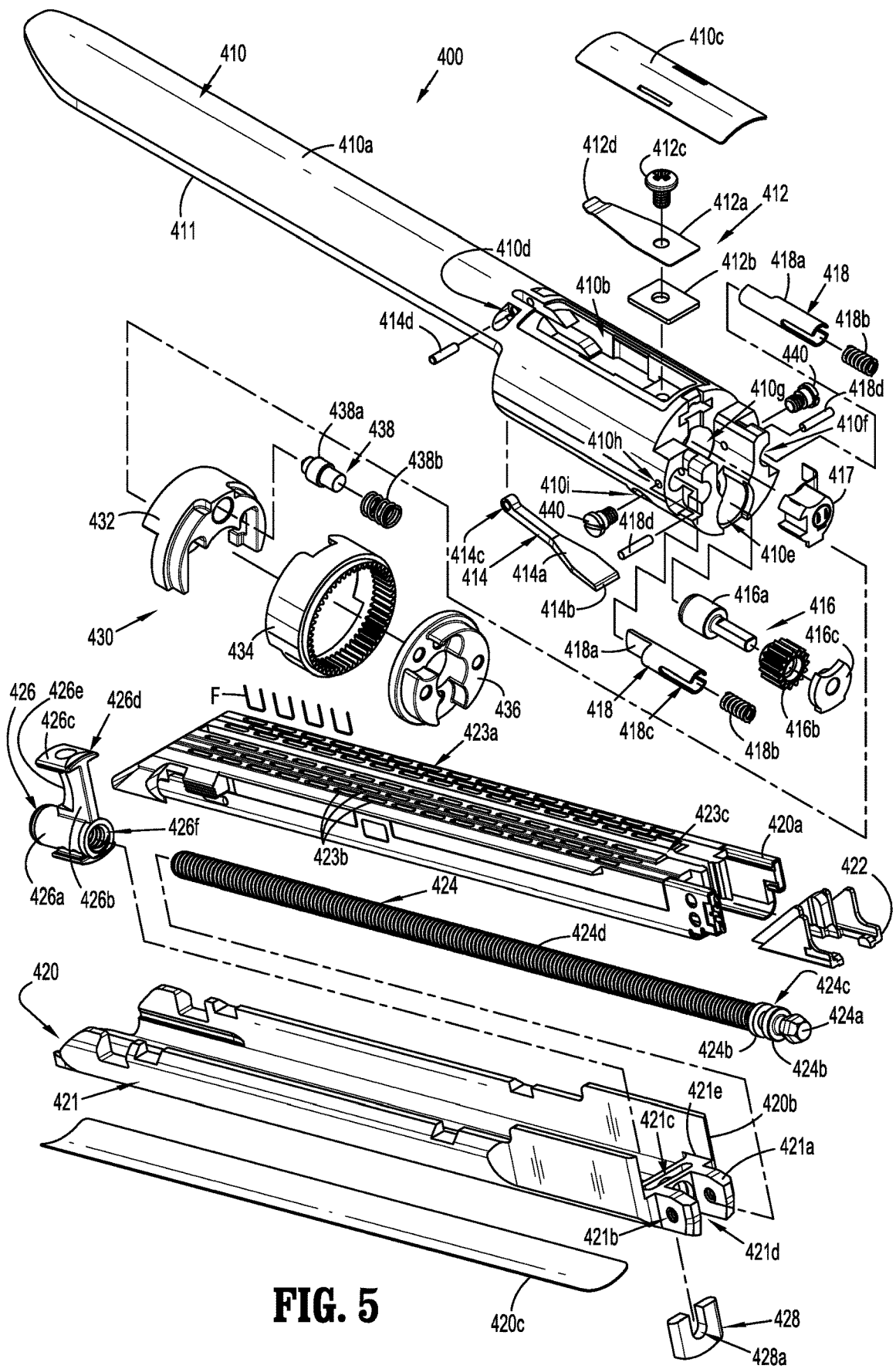
FIG. 5 is a perspective view, with parts separated, of the end effector of FIGS. 3 and 4.

With reference to FIG. 5, upper jaw member 410 includes an anvil body 410a with a fastener forming surface 411 including a plurality of staple forming pockets (not shown), arranged in longitudinally extending rows and configured to form the fasteners upon a firing of end effector 400, as appreciated by one skilled in the art. Anvil body 410a supports a leaf spring assembly 412 and a lever assembly 414 that are supported within a chamber 410b of body 410a. Leaf spring assembly 412 and lever assembly 414 are enclosed within chamber 410b by a cover 410c that is selectively removable from body 410a. Together, leaf spring assembly 412 and lever assembly 414 function to bias jaw assembly 415 in the unapproximated state and enable pivotal movement of the jaw assembly 415 between the approximated and unapproximated states as described in greater detail herein.

Leaf spring assembly 412 includes a leaf spring 412a that is mounted to body 410a at a first end of leaf spring 412a by a mounting plate 412b and a fastener 412c. Leaf spring 412a extends to an engagement tip 412d at a second end of leaf spring 412a that can have any suitable configuration such as a curvilinear scoop.

Lever assembly 414 includes a lever 414a that defines a pin channel 414c on one end thereof and a distal tip 414b on an opposite end thereof. Lever 414 is pivotally mounted to anvil body 410a by a pin 414d that is received through pin channel 414c of lever 414a and a pin channel 410d defined in anvil body 410a.

Anvil body 410a defines a plurality of bores on a proximal end of anvil body 410a including a drive bore 410e that receives a drive assembly 416, a pair of plunger bores 410f that receives a pair of plunger assemblies 418, and a electrical contact bore 410g that receives an electrical contact member 417 that functions to electrically communicate with instrument housing 102 when end effector 400 is secured to shaft assembly 200. Drive assembly 416 includes a drive member 416a, a gear member 416b coupled to drive member 416a, and a mounting plate 416c that supports drive member 416a and gear member 416b. Each plunger assembly of the pair of plunger assemblies 418 includes a plunger 418a that receives a spring 418b that functions to spring bias plunger 418a in a distal direction to facilitate securement of fastener cartridge 420a to cartridge assembly 420. Plunger 418a defines a pin slot 418c that receives a pin 418d to secure each plunger assembly within a respective one of the pair of plunger bores 410f when pin 418d is received within a pin channel 410h defined within anvil body 410a.

Lower jaw member 420 is configured and adapted to selectively receive fastener cartridge 420a. Fastener cartridge 420a includes a tissue engaging surface 423a that defines a plurality of rows of fastener retaining slots 423b adapted to support the plurality of fasteners "F" (and a plurality of staple pushers, not shown, but can be appreciated by those skilled in art). Fastener cartridge 420a also includes a longitudinally extending knife slot 423c disposed between pairs of rows of fastener retaining slots 423b that is adapted to enable drive beam 426 to axially translate therethrough.

Lower jaw member 420 includes a mounting member 420b, in the form of a channel, that supports fastener cartridge 420a and a base member 420c couplable to mounting member 420b. Mounting member 420b includes a mounting body 421 having a pair of wings 421a that extends proximally therefrom. The pair of wings 421a define a fastener channel 421b therethrough that is dimensioned to receive fasteners 440 advanced into a pair of passages 410i defined in upper jaw member 410 for securing upper jaw member 410 to lower jaw member 420. A slot 421c and a screw passage 421d are defined in a plate 421e of mounting body 421 positioned adjacent to the pair of wings 421a.

An actuation sled 422 is supported by lower jaw member 420 and is adapted to advance through fastener cartridge 420a to fire the plurality of fasteners supported with fastener cartridge 420a as one skilled in the art will appreciate. Lower jaw member 420 rotatably supports a drive screw 424 therein that extends substantially an entire length of lower jaw member 420. Drive screw 424 is threadably engaged with drive beam 426, which is axially slidably supported in lower jaw member 420 between proximal and distal positions in response to rotation of drive screw 424, as described in greater detail below. Drive screw 424 includes a multi-faceted head 424a, a pair of retention members 424b that define an annular channel 424c therebetween, and a distally extending threaded shaft 424d. Drive screw 424 extends through screw passage 421d so that a bracket 428, which defines a U-shaped channel 428a therethrough, secures drive screw 424 to mounting member 420b when bracket 428 is received in slot 421c and positioned within annular channel 424c. Bracket 428 and mounting member 420b cooperate to axially and lateral fix drive screw 424 in lower jaw member 420 while enabling drive screw 424 to rotate.

Drive beam 426 has a substantially I-shaped cross-sectional profile configured to progressively approximate lower jaw member 420 and upper jaw member 410 as drive beam 426 travels through knife slot 423c in fastener cartridge 420a. Drive beam 426 functions to axially displace actuation sled 422 through lower jaw member 420 and includes a retention foot 426a having an internally threaded bore 426f, a vertically oriented support strut 426b supported on retention foot 426a, and a lateral projecting member 426c formed atop support strut 426b. Lateral projecting member 426c defines a notch 426d formed in an upper surface thereof. Vertically oriented support strut 426b supports a knife 426e thereon that is adapted to cut tissue.

FIG. 5 illustrates that mounting portion 430 is secured to the proximal end portion of upper jaw member 410. Mounting portion 430 includes a first member 432, a second member 434, and a third member 436 that are coupled together and support a spring assembly 438. Spring assembly 438 includes a plunger 438a and a spring 438b.

Figure 6:
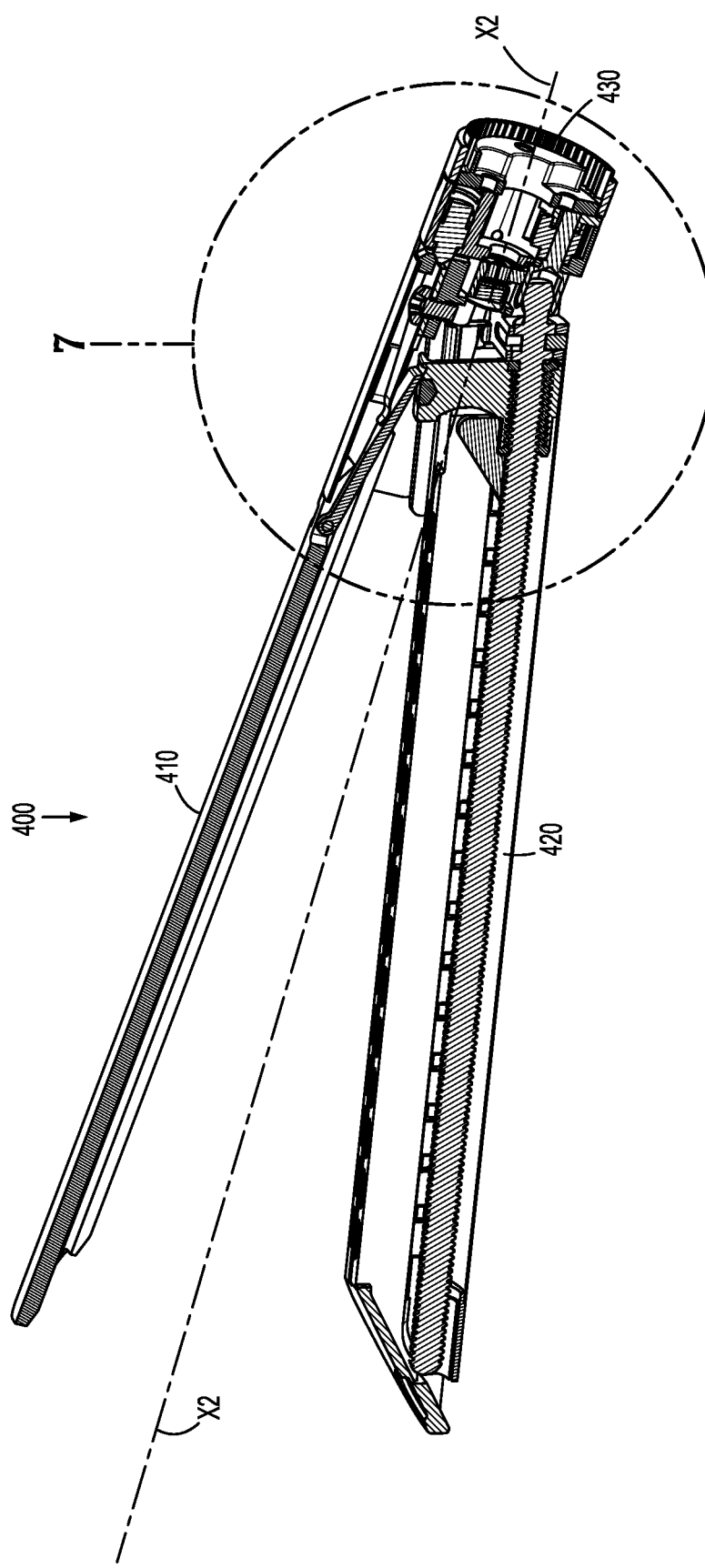
FIG. 6 is a side, cross-sectional, perspective view of the end effector of FIGS. 3-5, as taken through 6-6 of FIG. 4, showing the end effector in an unapproximated state.
Figure 7:
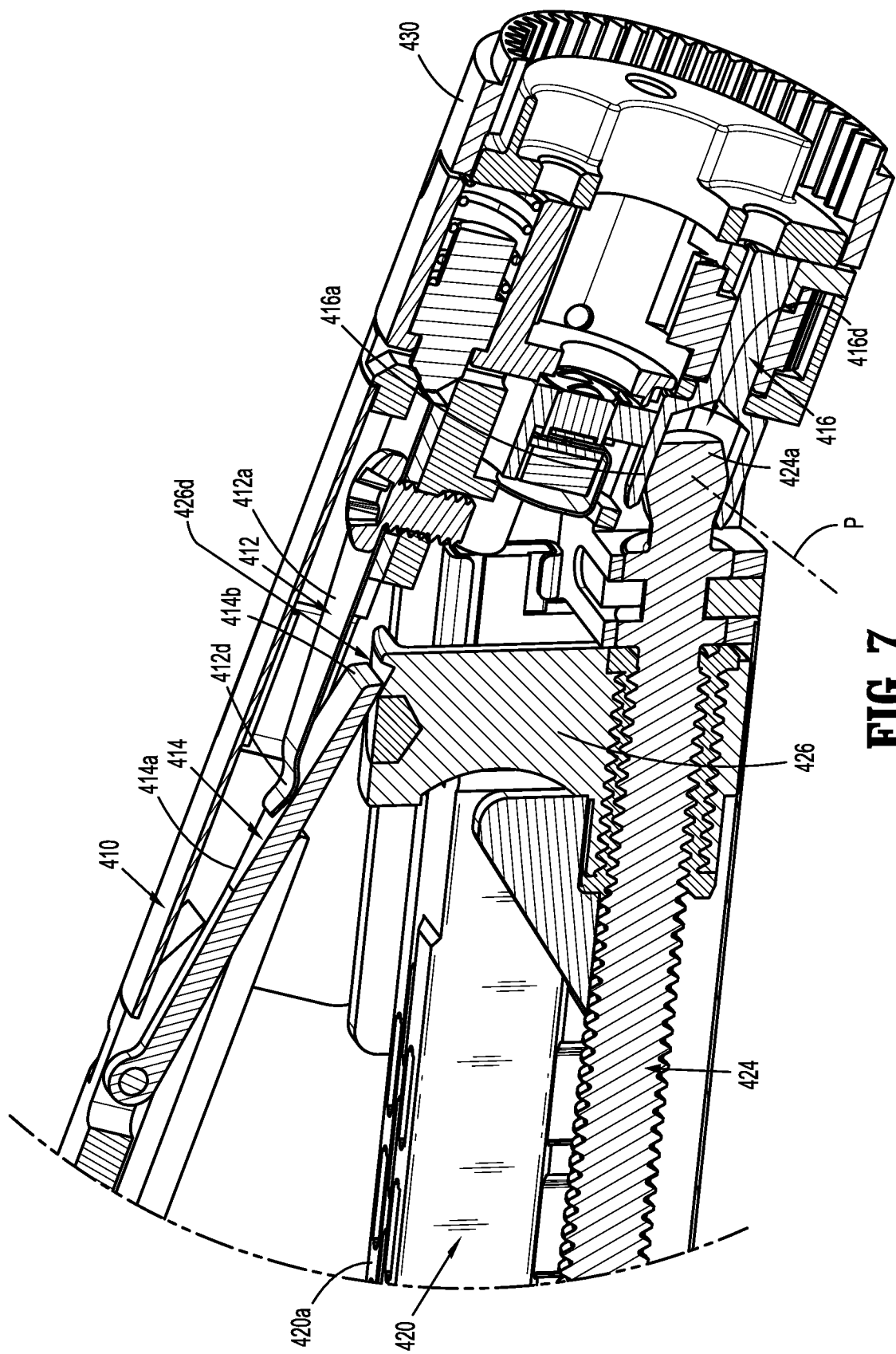
FIG. 7 is an enlarged view of the indicated area of detail shown in FIG. 6.

Referring now to FIGS. 6 and 7, end effector 400 is shown in an initial and/or unapproximated state, in which upper jaw member 410 is spaced from lower jaw member 420 relative to a longitudinal axis "X2" defined through end effector 400. In the unapproximated state, lower jaw member 420 is positioned at an acute angle (e.g., 15 degrees) relative to upper jaw member 410, drive screw 424 is disposed at an acute angle relative to mounting portion 430, and head 424a of drive screw 424 is supported at an acute angle within a bore 416d defined by drive member 416a.

As depicted in FIG. 7, when end effector 400 is in the unapproximated state, lever 414a is disposed in an extended position, due to spring biasing forces applied to lever 414a by leaf spring assembly 412, through contact with engagement tip 412d of leaf spring 412a. Drive beam 426 is disposed in a proximal-most position and leaf spring 412a of leaf spring assembly 412 is disposed in an unflexed state. In the extended position of lever 414a, distal tip 414b of lever 414a is disposed in notch 426d of lateral projecting member 426c of drive beam 426.

With reference to FIGS. 8 and 9, rotation of drive member 416a rotates head 424a of drive screw 424, which imparts rotation to drive screw 424. The pair of retention members 424b maintain drive screw 424 longitudinally fixed as the drive member 416a imparts rotational movement to drive screw 424. With drive screw 424 being threadably engaged with retention foot 426a of drive beam 426, rotational movement of drive screw 424 distally translates drive beam 426, as indicated by arrow "A." In this regard, distal tip 414b of lever 414a engages a notch sidewall 426g of drive beam 426, preventing distal translation of drive beam 426 and causing lower jaw member 420 to pivot relative to upper jaw member 410 in the direction indicated by arrow "B" and about a pivot axis "P" that is defined transversely through head 424a of drive screw 424. As lower jaw member 420 pivots toward upper jaw member 410, closing and/or approximating upper and lower jaw members 410, 420, drive beam 426 engages a bottom surface of lever 414a so that lever 414a pivots, counterclockwise (as illustrated in FIG. 9, albeit clockwise when viewed from the opposite side of end effector 400), toward upper jaw member 410 in the direction indicated by arrow "B" against spring biasing forces applied to a top surface of lever 414a through engagement tip 412d of leaf spring assembly 412. In response to pivoting movement of lever 414a toward upper jaw member 410, leaf spring 412a begins to flex to a flexed state in the direction indicated by arrow "B" so that leaf spring 412a pivots, clockwise (as illustrated in FIG. 9, albeit counterclockwise when viewed from the opposite side of end effector 400), relative to fastener 412c, toward upper jaw member 410.

Figure 10:
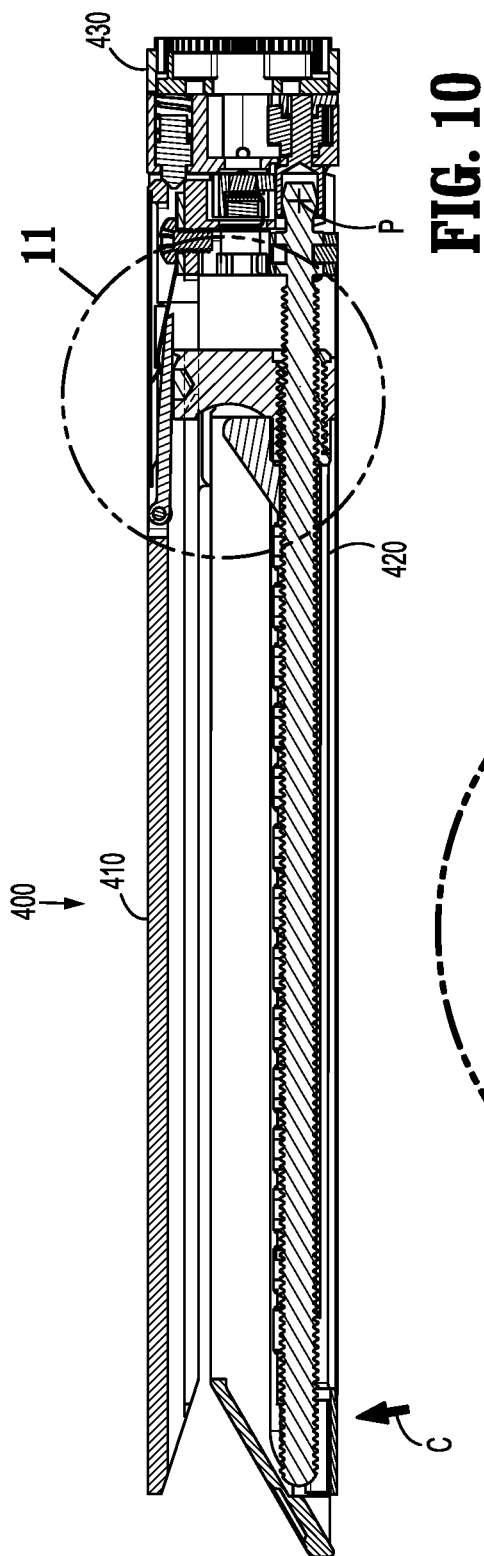
FIG. 10 is a side, cross-sectional view of the end effector in an approximated state with the drive beam thereof shown in a partially advanced position.
Figure 11:
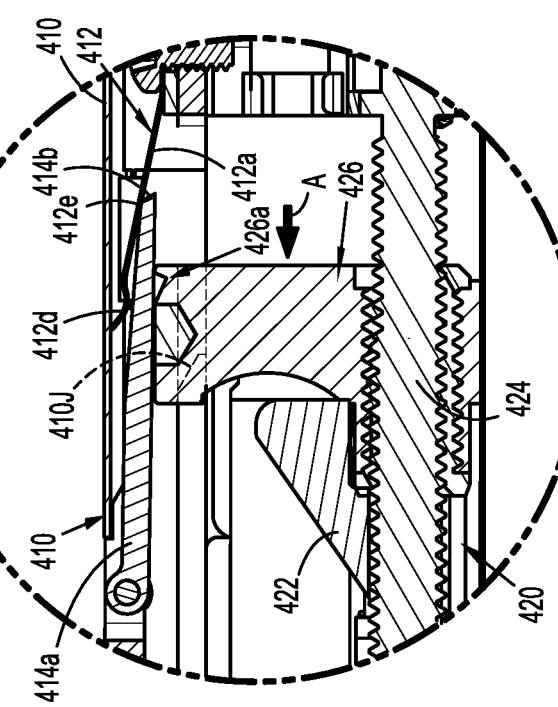
FIG. 11 is an enlarged view of the indicated area of detail shown in FIG. 10.

As seen in FIGS. 10 and 11, further rotational movement of drive screw 424 pivots lever 414a so that distal tip 414b of lever 414a separates from notch 426a enabling lever 414a to pivot toward a retracted position and enabling lower jaw member 420 to continue to pivot toward upper jaw member 410, as indicated by arrow "C," until upper and lower jaw members 410, 420 are positioned in the approximated state. Upon separation of distal tip 414b of lever 414a and notch 426a of drive beam 426, continued rotational movement of drive screw 424 distally translates drive beam 426, as indicated by the arrow "A," beneath lever 414a along the bottom surface of lever 414a or lever assembly 414. Distal translation of drive beam 426 drives lever 414a to the retracted position in which distal tip 414b engages a bottom surface of leaf spring 412a at a point 412e along leaf spring 412a, separating engagement tip 412d from a top surface of lever 414a.

Figure 12:
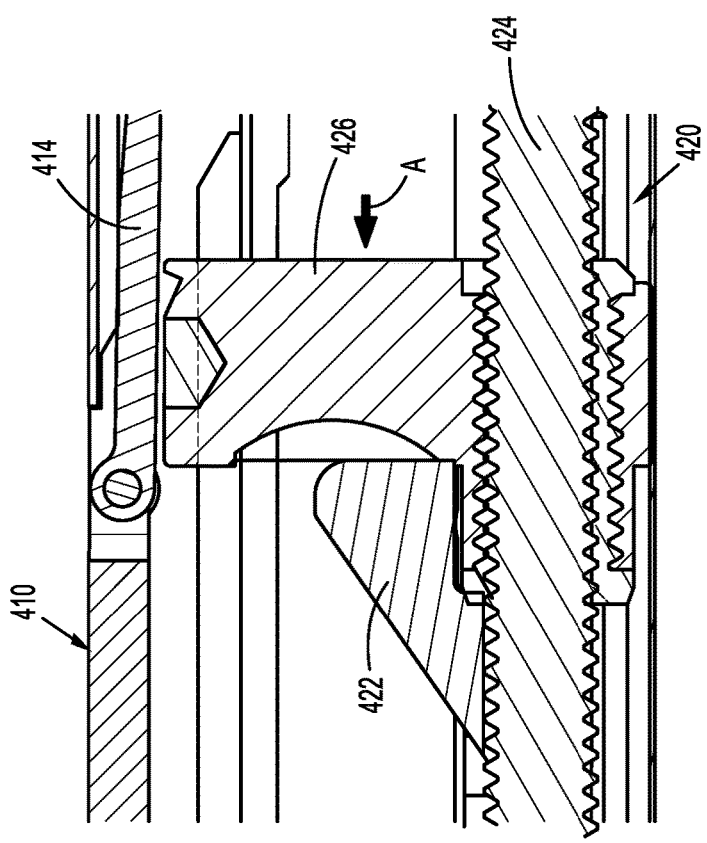
FIG. 12 is an enlarged, partial, cross-sectional view of the end effector showing the drive beam partially advanced.
Figure 13:
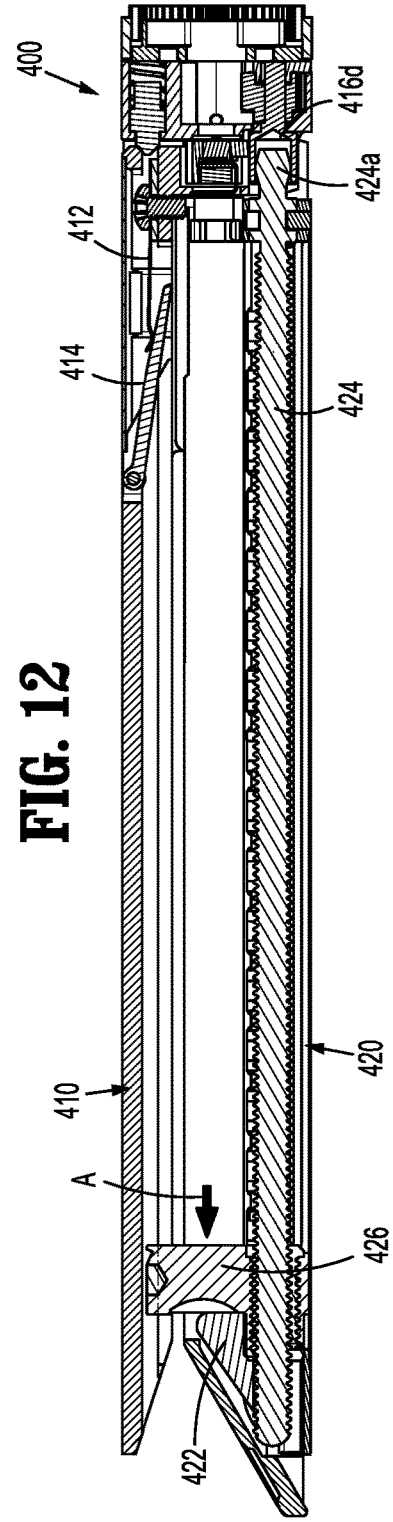
FIG. 13 a side, cross-sectional view of the end effector in an approximated state with the drive beam thereof shown in a distally advanced position.

With reference to FIGS. 12 and 13, when upper and lower jaw members 410, 420 are in the approximated state, lower jaw member 420 is positioned in parallel with upper jaw member 410, and head 424a of drive screw 424 is supported within a bore 416d of drive member 416a so that drive screw 424 is parallel to upper jaw member 410. In the approximated state, continued rotation of drive screw 424 distally translates drive beam 426 through end effector 400 toward a distal end portion of end effector 400, as indicated by arrow "A." Upon translating drive beam 426, distally past lever assembly 414, leaf spring assembly 412 urges lever assembly 414 to the extended position. Continued rotation of drive screw 424 advances actuation sled 422 through fastener cartridge 420a to fire the plurality of fasteners stored within fastener cartridge 420a for securing to tissue.

Drive screw 424 can then be rotated in an opposite direction to retract drive beam 426 proximally to the proximal-most position. More particularly, drive beam 426 is retracted proximally until drive beam 426 engages lever assembly 414, which under the spring bias of leaf spring assembly 412, urges upper and lower jaw members 410, 420 apart so that upper and lower jaw members 410, 420 are disposed in the original or unapproximated state as shown in FIG. 6. Fastener cartridge 420a can then be removed, disposed of, and/or replaced, as desired, and the operation of end effector 400 described above can be repeated as necessary with a new, un-fired fastener cartridge 420a loaded in lower jaw member 420.

In embodiments, end effector 400 supports one or more computer or microchips (not shown) that electrically communicate signals or identification codes to the controller and/or circuit board of surgical instrument 100. The signals or identification codes can indicate whether or not fastener cartridge 420a, or portions thereof, is at least partially fired, unfired, etc. The chip may store certain specification such as the cartridge size, staple arrangement, staple length, clamp-up distance. The chip may store a code that indicates that the end effector has been used to prevent reuse of an empty or previously used end effector. The chip may store a unique identification code for the end effector. The information on the chip may be encrypted to prevent tampering. Reference may be made to U.S. patent application Ser. No. 13/968,563, filed on Aug. 16, 2013 (now U.S. Pat. No. 9,636,112), the entire contents of which is incorporated herein by reference, for a detailed discussion of an exemplary end effector supporting one or more computer or microchips.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed:

1. An electrically-powered end effector, comprising:
   a first jaw member;
   a lever coupled to the first jaw member; and
   a second jaw member supporting a drive beam defining a notch therein, the notch selectively engageable by the lever to block relative movement between the first and second jaw members, and the notch selectively disengageable with the lever to facilitate relative movement between the first and second jaw members.

2. The electrically-powered end effector of claim 1, wherein at least one of the first or second jaw members is coupled to an electrical power source that is configured to electrically power at least one of the first or second jaw members.

3. The electrically-powered end effector of claim 1, wherein the drive beam is axially translatable along the first and second jaw members to move the first and second jaw members between an unapproximated state and an approximated state.

4. The electrically-powered end effector of claim 3, wherein the lever is engaged with the notch when the first and second jaw members are in the unapproximated state, when the drive beam is in a proximal position, and when the lever is in an extended position, wherein the lever is engaged with the notch of the drive beam to limit distal translation of the drive beam prior to the second jaw member pivoting relative to the first jaw member from the unapproximated state to the approximated state.

5. The electrically-powered end effector of claim 4, wherein the lever is configured to disengage from the notch as the lever pivots from the extended position to a retracted position in response to the second jaw member pivoting relative to the first jaw member from the unapproximated state to the approximated state.

6. The electrically-powered end effector of claim 5, wherein the drive beam is distally translatable when the first and second jaw members are in the approximated state and the lever is in the retracted position.

7. The electrically-powered end effector of claim 4, wherein the first jaw member supports a spring assembly, the spring assembly including a spring configured to contact the lever to bias the lever to the extended position.

8. The electrically-powered end effector of claim 1, wherein the second jaw member supports a drive screw operably associated with the drive beam to translate the drive beam as the drive screw rotates.

9. The electrically-powered end effector of claim 8, wherein the drive beam includes a retention foot that threadably receives the drive screw, the drive screw being coupled to a rotatable drive member, wherein rotation of the drive screw in the retention foot facilitates pivotal movement of the second jaw member relative to the first jaw member and translation of the drive beam through a fastener cartridge supported by the second jaw member.

10. The electrically-powered end effector of claim 8, wherein the drive screw has a head projecting from a proximal end portion thereof, the head defining a pivot axis therethrough, the pivot axis being transverse to a longitudinal axis of the end effector between proximal and distal end portions of the end effector, the second jaw member configured to pivot relative to the first jaw member about the pivot axis.

11. The electrically-powered end effector of claim 1, wherein the first jaw member defines a ramp, the drive beam being engagable with the ramp to pivot the first jaw member and the second jaw member and enable the drive beam to distally translate along the first and second jaw members.

12. The electrically-powered end effector of claim 1, wherein the drive beam supports a knife adapted to cut tissue as the drive beam translates along the first and second jaw members.

13. An electrically-powered surgical stapling apparatus, comprising:
    a handle assembly;
    a shaft assembly extending distally from the handle assembly; and
    an end effector selectively detachable from the shaft assembly, the end effector including:
      a first jaw member;
      a lever coupled to the first jaw member;
      a second jaw member; and
      a drive beam supported by the second jaw member and defining a notch selectively engagable by the lever to block relative movement between the first and second jaw members, and the notch selectively disengageable with the lever to facilitate relative movement between the first and second jaw members.

14. The electrically-powered surgical stapling apparatus of claim 13, wherein the handle assembly includes an electrical power source configured to electrically power actuation of the end effector.

15. The electrically-powered surgical stapling apparatus of claim 13, wherein the lever is engaged with the notch when the first and second jaw members are in an unapproximated state, when the drive beam is in a proximal position, and when the lever is in an extended position.

16. The electrically-powered surgical stapling apparatus of claim 15, wherein the lever is configured to disengage from the notch as the lever pivots from the extended position to a retracted position in response to the second jaw member pivoting relative to the first jaw member from the unapproximated state to an approximated state.

17. The electrically-powered surgical stapling apparatus of claim 16, wherein the drive beam is distally translatable when the first and second jaw members are in the approximated state and the lever is in the retracted position.

18. The electrically-powered surgical stapling apparatus of claim 13, wherein first jaw member supports a leaf spring configured to contact the lever to bias the lever to an extended position.

19. The electrically-powered surgical stapling apparatus of claim 13, wherein the second jaw member supports a drive screw operably associated with the drive beam to translate the drive beam as the drive screw rotates.

20. The electrically-powered surgical stapling apparatus of claim 19, wherein the drive beam includes a retention foot that threadably receives the drive screw, the drive screw being coupled to a rotatable drive member, wherein rotation of the drive screw in the retention foot facilitates pivotal movement of the second jaw member relative to the first jaw member and translation of the drive beam along first and second jaw members.

\* \* \* \* \*